US010966684B2

United States Patent
Daoura

(10) Patent No.: US 10,966,684 B2
(45) Date of Patent: Apr. 6, 2021

(54) METHOD AND APPARATUS FOR INTERACTIVE DISPLAY OF THREE DIMENSIONAL ULTRASOUND IMAGES

(71) Applicant: KONINKLIJKE PHILIPS N.V., Eindhoven (NL)

(72) Inventor: Marco J. Daoura, Bothell, WA (US)

(73) Assignee: KONINKLIJKE PHILIPS N.V, Eindhoven (NL)

( * ) Notice: Subject to any disclaimer, the term of this patent is extended or adjusted under 35 U.S.C. 154(b) by 657 days.

(21) Appl. No.: 14/368,107

(22) PCT Filed: Dec. 20, 2012

(86) PCT No.: PCT/IB2012/057533
§ 371 (c)(1),
(2) Date: Jun. 23, 2014

(87) PCT Pub. No.: WO2013/093837
PCT Pub. Date: Jun. 27, 2013

(65) Prior Publication Data
US 2014/0358002 A1  Dec. 4, 2014

Related U.S. Application Data

(60) Provisional application No. 61/579,900, filed on Dec. 23, 2011.

(51) Int. Cl.
*A61B 8/00* (2006.01)
*A61B 8/08* (2006.01)
(Continued)

(52) U.S. Cl.
CPC ............ *A61B 8/466* (2013.01); *A61B 8/0883* (2013.01); *A61B 8/462* (2013.01); *A61B 8/467* (2013.01);
(Continued)

(58) Field of Classification Search
CPC ........... A61B 8/466; A61B 8/462; A61B 8/00; A61B 8/08; A61B 8/483; A61B 8/467;
(Continued)

(56) References Cited

U.S. PATENT DOCUMENTS 5,589,957 A * 12/1996 Aritake .................. G02B 27/22
359/22
6,031,519 A   2/2000 O'Brien
(Continued)

FOREIGN PATENT DOCUMENTS

JP  2008513084 A  5/2008
JP  2009100996 A  5/2009
(Continued)

OTHER PUBLICATIONS

Tachiki et al. "Fast calculation method for spherical computer-generated holograms," May 20, 2006, Applied Optics, vol. 45, No. 15, pp. 3527-3533.*
(Continued)

*Primary Examiner* — Keith M Raymond
*Assistant Examiner* — Patrick M Mehl

(57) ABSTRACT

A medical imaging system comprises a three dimensional (3D) ultrasound system and a 3D holographic display system. The ultrasound system generates 3D ultrasound data that can be used to construct a 3D image of a patient. The display system displays the image in a 3D holographic form and comprises a touchless input interface that allows a user to control the display from within a sterile field while performing a medical procedure.

20 Claims, 4 Drawing Sheets

(51) Int. Cl.
*G03H 1/22* (2006.01)
*G03H 1/00* (2006.01)

(52) U.S. Cl.
CPC ............ *A61B 8/483* (2013.01); *G03H 1/2294* (2013.01); *G03H 2001/0061* (2013.01); *G03H 2210/30* (2013.01)

(58) Field of Classification Search
CPC ............... A61B 8/0883; G03H 1/2294; G03H 2210/30; G03H 2001/0061
See application file for complete search history.

(56) References Cited

U.S. PATENT DOCUMENTS

| | | | |
|---|---|---|---|
| 6,450,960 | B1 | 9/2002 | Rather |
| 8,500,284 | B2 | 8/2013 | Rotschild et al. |
| 2004/0046709 | A1 | 3/2004 | Yoshino |
| 2006/0020202 | A1* | 1/2006 | Mathew ............... A61B 8/463 600/437 |
| 2007/0055949 | A1 | 3/2007 | Thomas |
| 2009/0109215 | A1 | 4/2009 | Fein |
| 2009/0237759 | A1* | 9/2009 | Maschke ............... A61B 6/037 359/9 |
| 2009/0259960 | A1* | 10/2009 | Steinle ............... A61B 90/36 715/771 |
| 2009/0278915 | A1* | 11/2009 | Kramer ............... G06F 3/017 348/48 |
| 2009/0282371 | A1* | 11/2009 | Curl ............... G06F 19/327 715/863 |
| 2010/0050133 | A1* | 2/2010 | Nishihara ............... G06F 3/017 715/863 |
| 2010/0249589 | A1* | 9/2010 | Lysyansky ............... A61B 8/466 600/440 |
| 2010/0286519 | A1 | 11/2010 | Lee |
| 2011/0125026 | A1* | 5/2011 | Neto ............... A61B 8/06 600/463 |
| 2011/0282331 | A1* | 11/2011 | Brennan ............... A61B 3/102 606/4 |
| 2014/0361988 | A1* | 12/2014 | Katz ............... G06F 3/011 345/156 |

FOREIGN PATENT DOCUMENTS

| | | |
|---|---|---|
| JP | 2011527760 A | 11/2011 |
| WO | 2004109330 A1 | 12/2004 |
| WO | 2006030378 A1 | 3/2006 |
| WO | 2010004563 A1 | 1/2010 |
| WO | 2010076722 A1 | 7/2010 |

OTHER PUBLICATIONS

Favalora 2005 Computer 38:37-44 (Year: 2005).*
Grossman et al. 2004 Proc. 17th Annual ACM Symp UIST 2004:61-70 (Year: 2004).*

* cited by examiner

METHOD AND APPARATUS FOR INTERACTIVE DISPLAY OF THREE DIMENSIONAL ULTRASOUND IMAGES

TECHNICAL FIELD

The present invention is directed generally to medical imaging and display technologies. More particularly, various inventive methods and apparatus disclosed herein relate to the interactive display of three dimensional ultrasound images.

BACKGROUND

Ultrasound imaging is a medical technique used to observe subcutaneous body structures such as tendons, joints, muscles, vessels, and internal organs. Through the use of ultrasound imaging, clinicians are able to observe and diagnose various pathologies or lesions of these structures. They can also use ultrasound imaging to assist in various interventional or surgical procedures.

Echocardiography is a specific type of ultrasound imaging used to observe the heart. Echocardiography is most commonly performed by placing an ultrasound transducer, or probe, on the chest wall of a patient and using the probe to capture images through the chest wall. This is referred to as transthoracic echocardiography. An alternative to this approach is to pass an ultrasound probe into the patient's esophagus and perform heart imaging from within the esophagus. This is referred to as transesophageal echocardiography.

Echocardiography has traditionally been used to produce live images of two dimensional (2D) slices of the heart. However, recent advances in technology have allowed echocardiography to produce live images of the heart in three dimensions (3D). This is typically accomplished by an ultrasound probe having an array of imaging elements coupled to a processing system. The array of imaging elements captures multiple images in parallel, and the processing system combines the multiple images to construct a 3D image.

Live 3D echocardiography has various diagnostic applications, such as the observation of heart deformities and arrhythmias. In addition, live 3D echocardiography can be used as part of an interventional procedure, either before, during, or after the procedure—a practice referred to as peri-interventional echocardiography. Peri-interventional echocardiography can be used, for instance, to analyze anatomy before a procedure, to assist a clinician in guiding and placement of a catheter based device, and to assess the success of a procedure after the procedure is finished. Similarly, live 3D echocardiography can also be used as part of a surgical procedure, either before, during, or after the procedure—a practice referred to as peri-surgical echocardiography. Peri-surgical echocardiography can be used, for instance, to observe anatomy before cutting open the chest, to distinguish between a need to repair or replace a heart valve, and to determine intra-operative endpoints before closing the chest.

During a peri-interventional or peri-surgical procedure, live 3D echocardiography images can be displayed on a 2D screen to allow clinicians to observe different aspects of the heart. Moreover, the display can be controlled to change its properties, such as the 3D viewing angle, image contrast, or zoom. This is generally accomplished through the use of a computing interface such as a personal computer with a mouse and a keyboard.

In general, the clinician performing a peri-interventional or peri-surgical procedure is unable to control the display of the echocardiography images from within the sterile field in which the procedure is performed. This is due to various constraints on the clinician, such as a need to maintain sterile and unencumbered hands, and limited space for computer equipment. Accordingly, additional clinicians may be required to assist the clinician in changing the viewing properties of the images as needed. This can create complications, however, as it typically increases the number of people required to perform the procedure, increases the amount of communication required during the procedure, and adds steps to an already complicated procedural protocol.

Due to these and other shortcomings of conventional technologies, there is a need for improved methods and apparatus for interactive display of live 3D ultrasound images such as those used in echocardiography.

SUMMARY

The present disclosure is directed to inventive methods and apparatus for the interactive display of 3D ultrasound images. For example, in certain embodiments, a 3D ultrasound system is connected to a 3D holographic display system. The holographic display system displays 3D images constructed from ultrasound data, and it allows a user to control the display using touchless inputs such as hand gestures. For example, the user may rotate the viewing angle of a 3D image by moving a hand near the display in a direction of desired rotation.

The ability to control a holographic display system using touchless inputs allows a clinician to control the viewing properties of displayed images without contaminating a sterile field in which a peri-interventional or peri-surgical procedure is being performed. It can also lead to faster and more accurate control of the display, and it can reduce the number of clinicians required to assist in a procedure.

Generally, in one aspect, a method of displaying 3D ultrasound data comprises capturing the 3D ultrasound data using an ultrasound probe, communicating the ultrasound data to a 3D holographic display system and displaying the ultrasound data on the display system in real-time, receiving a touchless input from a user, and configuring the display of the ultrasound data on the display system based on the touchless input.

In some embodiments, configuring the display of the 3D ultrasound data comprises rotating, translating, or scaling a holographic image formed by the ultrasound data.

In some embodiments, the ultrasound data is echocardiography data captured in connection with a peri-interventional or peri-surgical echocardiography procedure. Moreover, in some embodiments, the display system is mounted above a subject of the procedure, for instance, on the ceiling of an interventional laboratory or a catheterization laboratory.

In some embodiments, the touchless input comprises a hand gesture, or a voice command.

In some embodiments, configuring the display of the ultrasound data on the display system based on the touchless input comprises transmitting a signal to the ultrasound probe to control a view of the ultrasound data captured by the ultrasound probe and shown on the display.

In another aspect, a medical imaging system comprises an ultrasound probe configured to capture 3D data from a subject, a processing system configured to generate live 3D images from the 3D data, a 3D holographic display system configured to display the live 3D images generated by the processing system, and a user interface configured to detect a touchless input from a user and to initiate an image transformation of the live 3D images in the display system in response to the touchless input.

In some embodiments, the image transformation comprises image rotation, translation, or scaling.

In some embodiments, the user interface comprises one or more electromagnetic field sensors configured to detect one or more hand gestures.

In some embodiments, the user interface comprises a computer vision system configured to detect one or more hand gestures.

In some embodiments, the ultrasound probe is a transesophageal echocardiography probe.

In some embodiments, the 3D holographic display system is mounted to a ceiling of an interventional laboratory, an operating room, or a catheterization laboratory.

In some embodiments, the processing system communicates with the display system through a wireless communication interface.

In some embodiments, the user interface is further configured to initiate recording or playback of a stream of images, pausing of an image display, or operation of a menu system in response to hand gestures.

In another aspect, a method of performing a peri-interventional or peri-surgical medical procedure within a sterile field comprises applying an ultrasound probe to a patient, observing a 3D ultrasound image derived from data generated by the ultrasound probe and displayed on a 3D holographic display device, treating the patient based on the observation, and controlling the 3D holographic display device through a touchless interface.

In some embodiments, treating the patient comprises applying a catheter based device to the patient or performing surgery on the patient.

In some embodiments, the touchless interface comprises one or more electromagnetic sensors configured to detect one or more hand gestures.

In some embodiments, controlling the 3D holographic display device comprises performing a hand gesture to modify viewing properties of a 3D image presented on the 3D holographic display device.

In some embodiments, modifying the viewing properties of the 3D image comprises rotating, scaling, or translating the 3D image.

As used herein for purposes of the present disclosure, the following terms should be interpreted as follows.

The term "ultrasound data" denotes information generated through the use of ultrasound technology. Ultrasound data typically comprises raw measurements that can be used to generate ultrasound images. For example, 3D ultrasound data can comprise measurement values associated with particular 3D locations of a subject.

The term "ultrasound probe" denotes an instrument that generates ultrasound data in relation to a subject being measured, such as a patient. An ultrasound probe typically comprises a transducer that uses ultrasound waves to generate raw measurements of the subject when placed in proximity to the subject. Ultrasound probes can vary in shape and size, and they can have different types and configurations of sensing elements.

The term "3D holographic image" denotes an assembly of light creating a visual representation of a subject in volumetric space. A 3D holographic image can be created, for instance, by controlling or manipulating laser light, e.g., by reflection, diffraction, or superposition.

The term "3D holographic display system" denotes technology for creating a 3D holographic image. In some embodiments, a 3D holographic display system comprises a container or substrate in which such an image is formed. However, a 3D holographic display system is not limited to such configurations. In addition, in certain embodiments, a 3D holographic display system comprises components for controlling viewing properties of 3D holographic images. Such components can be located proximate to the image display or they can be placed in a different location.

The term "touchless input" denotes a mechanism allowing a user to communicate with a system without physical contact. For example, a touchless input can comprise a hand gesture or a voice command. The term "touchless input" should not be interpreted to preclude all physical contact in a particular input operation, but rather it merely indicates the presence of a non-contact input mechanism. The term "hand gesture" denotes a type of touchless input in which a particular movement or configuration of a user's hand defines an input value. For instance, a sweeping motion of a user's hand may define an input value that controls an image display to rotate an image.

The term "touchless input interface" denotes a mechanism allowing a system to receive touchless inputs. For instance, in some embodiments, a 3D holographic display system comprises a touchless input interface that senses an electromagnetic field in its environment to determine whether a user has performed a particular hand gesture. Alternatively, a touchless input interface could use optical transistors or various computer vision techniques to detect particular gestures. The term "touchless input interface" should not be interpreted to preclude all physical contact with the interface, but rather it merely indicates the presence of a mechanism or mechanisms for receiving touchless inputs.

The term "image transformation" denotes a change in the display or viewing properties of an image. For instance, an image transformation can include linear transformations such as rotation, translation, or scaling, or it can involve more complex transform functions.

The term "peri-interventional procedure" denotes a medical procedure performed before, during, or after a medical intervention within a sterile field, and the term "peri-surgical procedure" denotes a medical procedure performed before, during, or after surgery within a sterile field.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION

As discussed above, conventional technologies for displaying 3D ultrasound images suffer from a variety of shortcomings that can complicate and impede medical procedures. For instance, in order to maintain a sterile field while performing a procedure, conventional technologies typically require one clinician to control the display of images while another clinician manipulates ultrasound instruments, and yet another clinician performs the procedure. This tends to increase the number of steps and the amount of communication required to perform a procedure. It also reduces the amount of control by the clinician performing the procedure.

Applicants have therefore recognized and appreciated that it would be beneficial to provide methods and apparatuses allowing a clinician to control the display of 3D ultrasound images from within the sterile field. For example, Applicants have recognized the benefits of displaying 3D ultrasound images using a 3D holographic display system that can be controlled using touchless inputs such as hand gestures. Such methods allow the clinician to control the display from within the sterile field, and they can also provide the clinician with more precise and direct control over the display, which can lead to more efficient and accurate procedures.

In view of the foregoing, various embodiments and implementations of the present invention are directed to systems and methods for interactive display of 3D ultrasound images using a 3D holographic display system. The 3D holographic display system is controlled through a touchless interface that allows a clinician to change the viewing properties of displayed images through hand gestures, voice commands, or other types of inputs that do not require the clinician to leave the sterile field. Accordingly, the described methods and systems can be readily used in the context of medical procedures requiring a sterile field, such as peri-interventional or peri-surgical procedures.

Certain embodiments are particularly relevant to procedures involving echocardiography. For instance, certain embodiments can be applied to echocardiography procedures performed in a catheterization laboratory or an interventional laboratory. In such procedures, a clinician such as an invasive cardiologist may control a 3D holographic display system of ultrasound data generated through transthoracic or transesophageal echocardiography while inserting an instrument such as a catheter into the subject. This control can be performed through a touchless interface, allowing the clinician to modify the displayed images without contaminating the sterile field.

Figure 1:
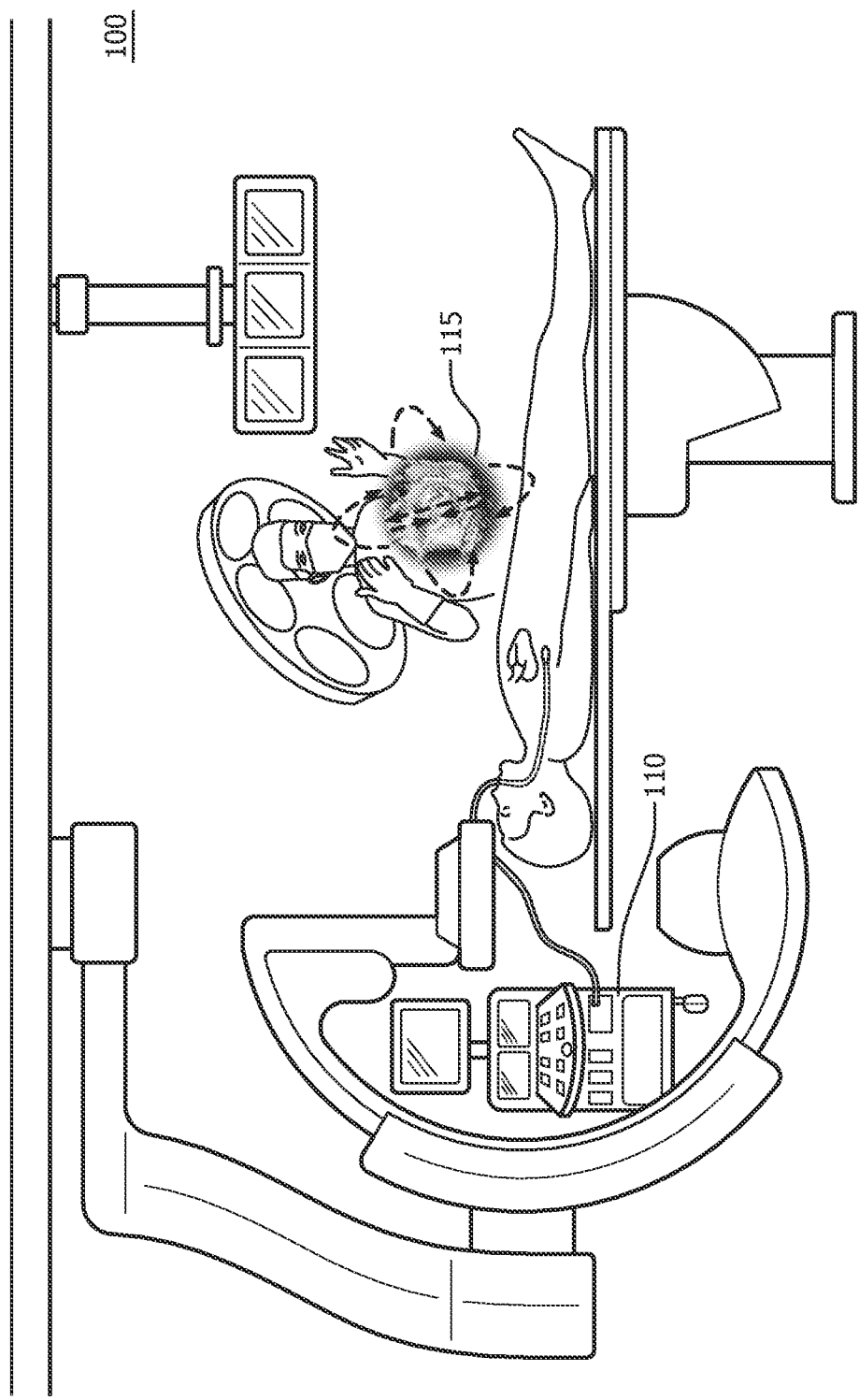
FIG. 1 illustrates an ultrasound system and a 3D holographic display system being used for a transesophageal echocardiogram according to an example embodiment.

FIG. 1 illustrates an ultrasound system and a 3D holographic display system being used for a transesophageal echocardiogram according to an example embodiment. These systems are shown in the context of a cardiac catheterization (cath) lab 100 in which a clinician performs a procedure from within a sterile field. These systems, however, can be used in many other contexts, such as an operating room, a data reviewing room, an interventional lab, and others.

Referring to FIG. 1, the ultrasound system comprises an ultrasound probe 105 connected to a processing system 110. The clinician places ultrasound probe 105 in a patient's esophagus near the heart. Ultrasound probe 105 uses ultrasound waves to generate data representing a 3D image of the patient's heart. The data is transmitted to processing system 110, which constructs a 3D image and then transmits the 3D image to a 3D holographic display system 115.

3D holographic display system 115 is located in front of the clinician to allow real-time visualization of the patient's heart during a medical procedure. In the example of FIG. 1, 3D holographic display system 115 has a spherical display suspended in air. This display can be generated, for example, by projecting beams of intersecting light in front of the clinician. These beams can be generated, for example, by lasers mounted on various parts of cath lab 100.

As an alternative to the display shown in FIG. 1, 3D holographic display system 115 can be formed with a designated display medium such as a container, rather than forming a holographic image in mid air. For example, the display can take the form of a cylindrical container that produces a 3D holographic image through the use of light sources located within the cylinder. Such a cylindrical display can be mounted on the ceiling or a wall of cath lab 100 in proximity to the clinician to allow for convenient viewing during a procedure. In still other embodiments, the 3D holographic display system can be formed in a configuration other than a cylinder or a floating sphere. Moreover, it is not required to have a unitary form factor. For instance, it could be formed of dispersed components that function together to create the holographic image in air or within a container or designated medium. One commercially available example of a 3D holographic device using a container is Sony's Raymodeler.

3D images in 3D holographic display system 115 can typically be viewed simultaneously from any 360 degree orientation. Accordingly, during certain medical procedures, one or more additional clinicians may observe the patient's heart from different angles. This can be beneficial, for instance, in precisely orienting an instrument, or monitoring heart health throughout the procedure.

3D holographic display system 115 also has a user interface that allows the clinician to control the display using touchless inputs such as hand gestures, poses, or voice commands, as indicated by arrows around 3D holographic display system 115. For instance, in some embodiments, the clinician can wave a hand across the outside of 3D holographic display system 115 to rotate the viewing angle of the heart. Because the clinician can control 3D holographic display system 115 without touching it, the clinician can perform such control operations without contaminating the sterile field around the patient. The user interface can be implemented using various technologies, such as electromagnetic field sensors, a computer vision system, or others. In some embodiments, the clinician can also use touchless inputs to control movement of ultrasound probe 105 through the interface of 3D holographic display system 115. For example, the clinician can use hand gestures on the interface to cause ultrasound probe 105 to move to a different portion of the esophagus wall or rotate to capture a different view of the heart. By controlling movement of ultrasound probe 105, the clinician can potentially obtain clearer images or more relevant views for a procedure being performed. In order to facilitate such control, the ultrasound system may be equipped with two way communication or other feedback mechanisms between 3D holographic display system 115 and ultrasound probe 105 or processing system 110.

In an invasive cardiac procedure using conventional technology, an echocardiologist may work the ultrasound equipment and maneuver the transesophageal probe while a technician controls a display system and an interventional cardiologist performs a procedure. However, through the use of the touchless interface of 3D holographic display system 115, the echocardiologist or interventional cardiologist may be able to control the display, potentially eliminating the need for the additional technician. In addition, this can give the interventional cardiologist more power to control the displayed image and improve the procedures being performed.

As an example, in an invasive procedure, the interventional cardiologist may be wearing gloves covered with blood. Nevertheless, by performing hand gestures around the 3D holographic display system 115, the cardiologist can reconfigure the displayed images without contaminating the gloves or dirtying the device. As the cardiologist inserts a catheter, the display can be rotated to a viewing angle and zoom level allowing precise observation of the catheter's positioning. Later, the display can be oriented to confirm that there is no unwanted leakage before the body is closed and the procedure is completed.

Although FIG. 1 shows a physician using 3D holographic display system 115 during the course of an interventional or surgical procedure, it can also be used throughout peri-interventional and peri-surgical procedures. For instance, after a clinician has taken steps to sterilize his or her hands, etc., certain tasks may be performed using 3D holographic display system 115 from within the sterile field before an invasive procedure is performed, such as reviewing stored images using hand gestures. Moreover, the touchless interface of 3D holographic display system 115 allows it to be used in environments where conventional technologies are typically not used. For instance, a physician may use 3D holographic display system 115 within a data reviewing room after sterilizing his or her hands because the use of this system does not require touching anything in the data reviewing room.

Figure 2:
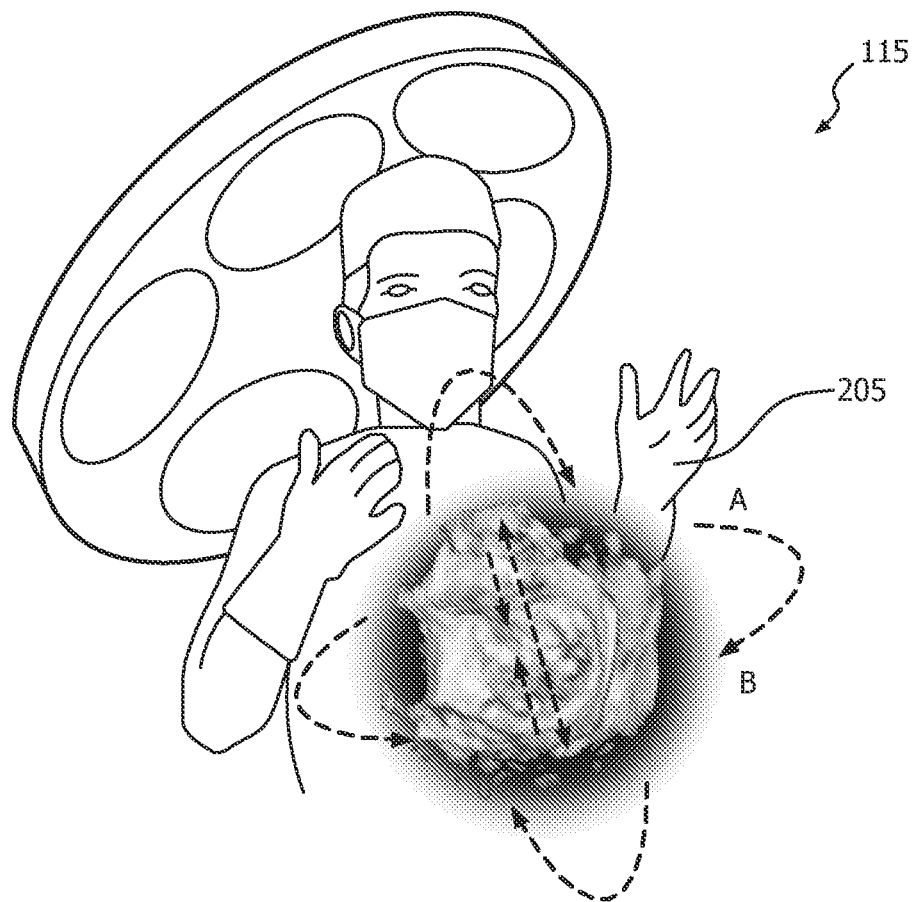
FIG. 2 illustrates a gesture being performed to control viewing properties of the 3D holographic display system of FIG. 1 according to an example embodiment.

FIG. 2 illustrates a gesture being performed to control viewing properties of the 3D holographic display system of FIG. 1 according to an example embodiment. The example of FIG. 2 is one of many gestures that could be performed by holographic display system 115.

Referring to FIG. 2, a simple hand gesture is performed by moving a hand 205 in a sweeping motion from point "A" to point "B" around a circumference of holographic display system 115. A touchless interface of the device detects the movement and causes a 3D image of the heart to rotate about a vertical axis shown at the center of the 3D display. The clinician can also control the rotation of the display in other dimensions using gestures indicated by arrows in FIG. 2.

In addition to controlling the rotation of the 3D image, hand gestures can also be used to control other viewing properties, such as zooming, movement of the image left/right or up/down. Moreover, hand gestures can also be used to control other functions of holographic display system 115, such as recording and playback of a stream of images, deleting previously recorded images, pausing the image display, operation of a menu system, and so on.

Figure 3:
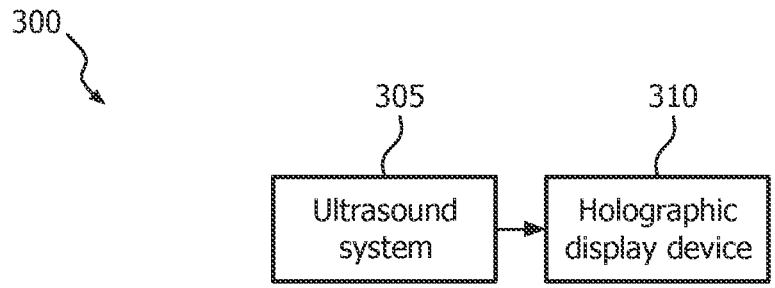
FIG. 3 illustrates a system comprising an ultrasound system and a holographic display system according to an example embodiment.

FIG. 3 illustrates a system 300 comprising a 3D ultrasound system 305 and a 3D holographic display system 310 according to an example embodiment. System 300 represents a more generalized version of the system shown in FIG. 1.

In general, 3D ultrasound system 305 can comprise any type of ultrasound equipment capable of generating 3D ultrasound data. It can be configured to generate a 3D image from the ultrasound data, or it can transmit the ultrasound data to another component, such as 3D holographic display system 310, to form a 3D image. Similarly, 3D holographic display system 310 can comprise any type of equipment capable of producing 3D holographic images from 3D ultrasound data and allowing control of the display through the use of touchless inputs.

Ultrasound system 305 and holographic display system can be integrated with each other using a variety of techniques or technologies. For instance, they can be designed to communicate using a standardized wireless or wired communication protocol, such as WiFi, Bluetooth, USB, firewire, PCI-E, and so on. In addition, they can be designed to use a compatible data format for convenient integration.

Figure 4:
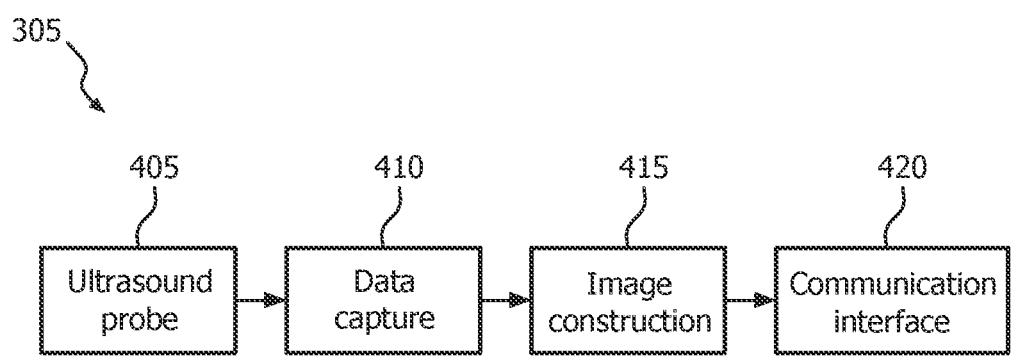
FIG. 4 illustrates an example of the ultrasound system of FIG. 3 according to an example embodiment.

FIG. 4 illustrates an example of ultrasound system 305 of FIG. 3 according to an example embodiment.

Referring to FIG. 4, ultrasound system 305 comprises an ultrasound probe 405, a data capture unit 410, an image construction unit 415, and a communication interface 420. Ultrasound probe 405 comprises a transducer array configured to generate 3D ultrasound data through the use of ultrasound waves. Data capture unit 410 captures and/or digitizes the 3D ultrasound data and transmits it to image construction unit 415. Image construction unit 415 processes the 3D ultrasound data to generate a 3D image. The image can be beneficially created in a format compatible with holographic display system. Once the 3D image is created, it is transmitted to communication interface 420, which then transmits the image to holographic display system. The elements shown in FIG. 4 typically perform their functions in real time in order to generate live 3D images. Accordingly, to facilitate efficient processing, they can be implemented using various pipelined and/or parallel processing technologies.

Figure 5:
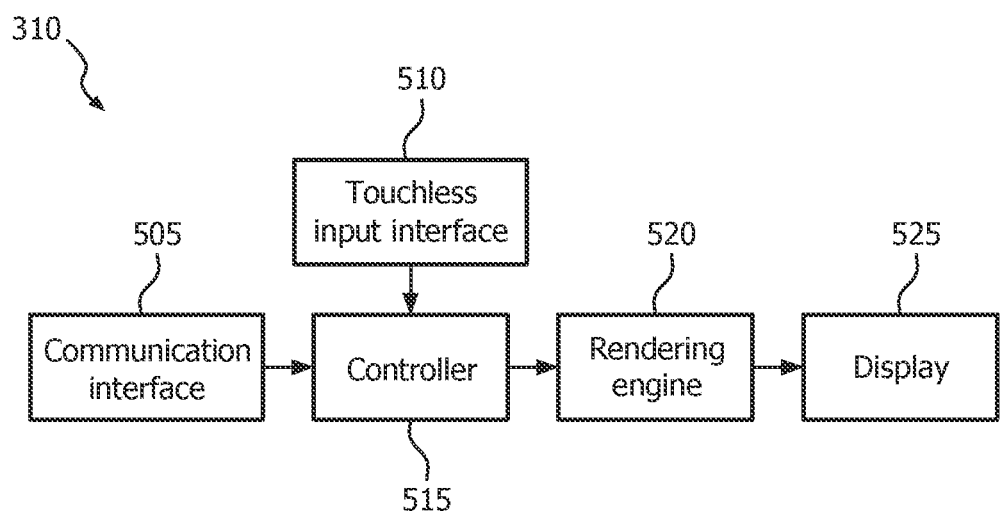
FIG. 5 illustrates an example of the holographic display system of FIG. 3 according to an example embodiment.

FIG. 5 illustrates an example of holographic display system 310 of FIG. 3 according to an example embodiment.

Referring to FIG. 5, holographic display system comprises a communication interface 505, a touchless input interface 510, a controller 515, a rendering engine 520, and a display 525. Communication interface 505 receives data from ultrasound system 305 and transmits the received data to controller 515. The data typically represents a 3D ultrasound image such as a 3D echocardiogram. Communication interface 505 can be implemented using any of various wired or wireless communication protocols. Touchless input interface 510 receives touchless inputs from a user and communicates the received inputs to controller 515. Such inputs can comprise, for instance, hand gestures or voice commands. Touchless input interface 510 can be implemented by various available sensing technologies, such as an array of electromagnetic field sensors, a camera-based computer vision system, or one or more microphones.

Controller 515 receives 3D image data from communication interface 505, and it receives touchless input data from touchless input interface 510. Based on this received information, controller 515 transmits data and/or commands to rendering engine 520 to cause it to render the image data.

Rendering engine 520 typically performs image transformations and other operations to render the 3D image data on display 525. The 3D image data is then displayed by display 525.

Figure 6:
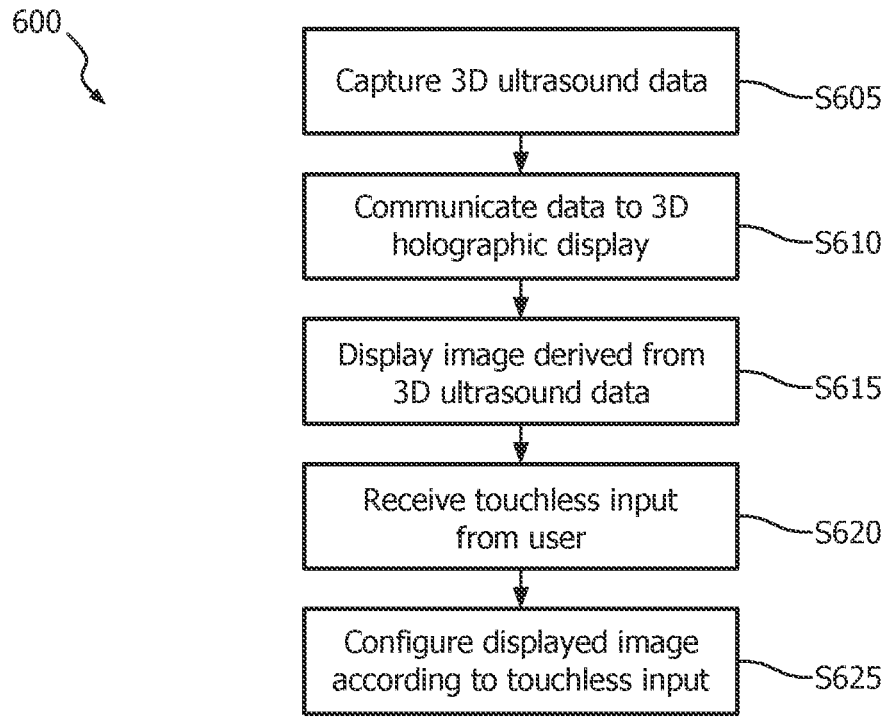
FIG. 6 illustrates a method of operating the system of FIG. 3 according to an example embodiment.

FIG. 6 illustrates a method 600 of operating the system of FIG. 3 according to an example embodiment. In the description that follows, example method steps are indicated by parentheses (SXXX).

Referring to FIG. 6, the method comprises capturing 3D ultrasound data (S605). As described above, this can be accomplished using an ultrasound probe, e.g., in a transthoracic echocardiogram or a transesophageal echocardiogram. Next, the captured data is communicated to a 3D holographic display system (S610). Thereafter, the 3D holographic display system displays a 3D image derived from the captured 3D ultrasound data (S615). Then, the 3D holographic display system receives a touchless input from a user, such as a clinician (S620). Finally, the displayed image is configured according to the touchless input (S625). The configuration of the displayed image can be performed, for instance, by performing an image transformation such as rotation, translation, or scaling according to the touchless input. Alternatively, the configuration of the displayed image can be changed by modifying the positioning of the ultrasound probe to modify the view of a captured image. For example, in response to a touchless input such as a sweeping hand gesture, the holographic display system may transmit a control system to the ultrasound system, causing it to transmit a signal to the ultrasound probe to control the (x, y, z) location of a transducer tip within a patient's esophagus. This can change the view of the ultrasound data captured by the ultrasound probe and shown on the display. For example, it can change the portion of the heart seen in the image, or it can generate a clearer image of the viewed portion. Those skilled in the art will recognize that there are many ways to control the view captured by the ultrasound probe, so a detailed description of the various alternative techniques will be omitted for the sake of brevity.

Figure 7:
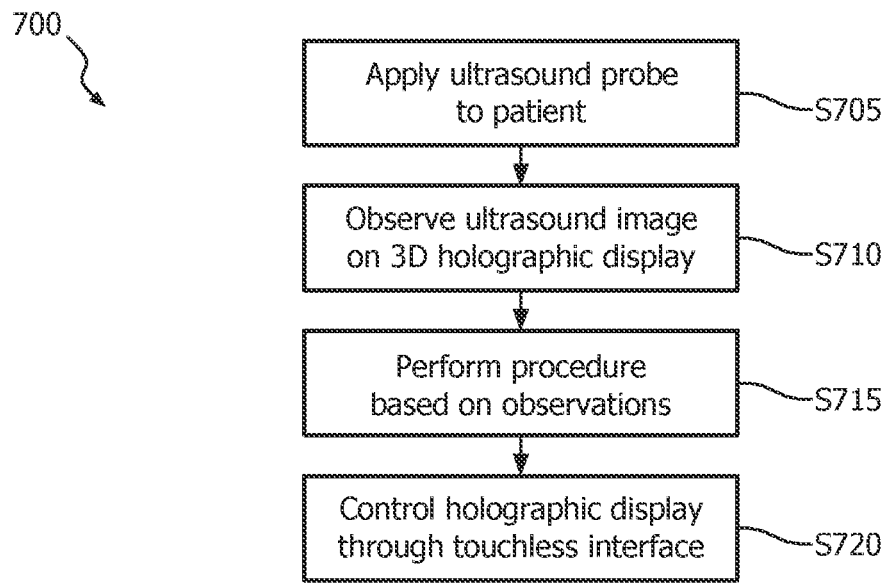
FIG. 7 illustrates a method of performing a medical procedure using the system of FIG. 4 according to an example embodiment.

FIG. 7 illustrates a method 700 of performing a medical procedure using system 300 of FIG. 3 according to an example embodiment.

Referring to FIG. 7, the method comprises applying an ultrasound probe to a patient to generate a 3D ultrasound image, such as an echocardiogram (S705). Next, the method comprises observing the 3D ultrasound image on a 3D holographic display (S710), performing a procedure based on the observations (S715), and controlling the holographic display through a touchless interface (S720). The method of FIG. 7 is generally performed by a clinician within a sterile field. For example it can be performed in an operating room, an interventional laboratory, or a catheterization laboratory during various invasive procedures. As indicated by the above description, the method of FIG. 7 can improve the clinician's control of the display, and it can lead to more efficient procedures.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The invention claimed is:

1. A medical imaging system, comprising:
   an ultrasound probe configured to capture three dimensional (3D) ultrasound data from a subject;
   an ultrasound processing system comprising one or more hardware processors configured by machine readable instructions to generate live 3D images from the 3D ultrasound data;
   a 3D holographic display system configured to display the live 3D images as a hologram suspended in space proximate to the subject; and
   a touchless input user interface configured to detect a touchless input from a user and facilitate an image transformation of the live 3D images in the hologram in response to the touchless input,
   wherein the touchless input comprises a detectable hand gesture along a portion of a circumference of the hologram,
   wherein the detectable hand gesture along the portion of the circumference causes a corresponding rotation of the hologram about one or more axes along a path that corresponds to the detectable hand gesture such that the hologram rotationally tracks a corresponding direction of the detectable hand gesture,
   wherein, responsive to detecting the touchless input, the touchless input user interface facilitates image transformation of the live 3D images by transmitting a control signal to the ultrasound probe to control a view of the ultrasound data captured by the ultrasound probe.

2. The medical imaging system of claim 1, wherein the image transformation comprises one or more of: image rotation, translation, or scaling.

3. The medical imaging system of claim 1, wherein the touchless input user interface comprises one or more electromagnetic field sensors configured to detect the hand gesture along the portion of the circumference of the hologram.

4. The medical imaging system of claim 1, wherein the user interface comprises a computer vision system comprising a camera, the computer vision system configured to detect one or more hand gestures along the portion of the circumference of the hologram.

5. The medical imaging system of claim 1, wherein the ultrasound probe is a transesophageal echocardiography probe.

6. The medical imaging system of claim 1, wherein the 3D holographic display system is configured to be mounted to a ceiling of an interventional laboratory, an operating room, or a catheterization laboratory.

7. The medical imaging system of claim 1, wherein the ultrasound processing system communicates with the 3D holographic display system through a wireless communication interface.

8. The medical image system of claim 1, wherein the touchless input user interface is configured to detect additional hand gestures, and wherein the additional hand gestures comprise one or more gestures that control viewing properties of the hologram.

9. The medical image system of claim 8, wherein the viewing properties comprise one or more of pan and zoom properties.

10. The medical image system of claim 1, wherein the touchless input user interface is configured to detect additional hand gestures, and wherein the additional hand gestures comprise one or more gestures that control operations of additional components of the system.

11. The medical imaging system of claim 1, wherein the 3D holographic display system further comprises a container comprising a display medium, wherein the container comprises light sources located within the container that are configured to produce the hologram.

12. A medical imaging system, comprising:
   an ultrasound probe configured to capture three dimensional (3D) ultrasound data from a subject;
   an ultrasound processing system comprising one or more hardware processors configured by machine readable instructions to generate live 3D images from the 3D ultrasound data;
   a 3D holographic display system configured to display the live 3D images as a hologram suspended in space proximate to the subject; and
   a touchless input user interface configured to detect a first touchless input from a user and facilitate an image transformation of the live 3D images in the hologram suspended in space in response to the first touchless input,
   wherein the first touchless input comprises a detectable hand gesture along a portion of a circumference of the hologram,
   wherein the hand gesture along the portion of the circumference of the hologram causes a corresponding rotation of the hologram about one or more axes along a path that corresponds to the detectable hand gesture such that the hologram rotationally tracks a corresponding direction of the detectable hand gesture,
   wherein, responsive to detecting the first touchless input, the touchless input user interface facilitates image transformation of the live 3D images by transmitting a control signal to the ultrasound probe to control a view of the ultrasound data captured by the ultrasound probe, and
   wherein the touchless input user interface is further configured to initiate recording of a stream of images responsive to detecting a second touchless input, and wherein the touchless input user interface is configured to pause an image display responsive to detecting a third touchless input.

13. The medical imaging system of claim 12, wherein the 3D holographic display system further comprises a container comprising a display medium, wherein the container comprises light sources located within the container that are configured to produce the hologram.

14. The medical imaging system of claim 12, wherein the image transformation comprises one or more of: image rotation, translation, or scaling.

15. The medical imaging system of claim 12, wherein the touchless input user interface comprises one or more electromagnetic field sensors configured to detect the hand gesture along the portion of the circumference of the hologram.

16. The medical imaging system of claim 12, wherein the user interface comprises a computer vision system comprising a camera, the computer vision system configured to detect one or more hand gestures along the portion of the circumference of the hologram.

17. The medical imaging system of claim 12, wherein the 3D holographic display system is configured to be mounted to a ceiling of an interventional laboratory, an operating room, or a catheterization laboratory.

18. The medical imaging system of claim 12, wherein the ultrasound processing system communicates with the 3D holographic display system through a wireless communication interface.

19. The medical image system of claim 12, wherein the touchless input user interface is configured to detect additional hand gestures, and wherein the additional hand gestures comprise one or more gestures that control viewing properties of the hologram.

20. The medical image system of claim 19, wherein the viewing properties comprise one or more of pan and zoom properties.

* * * * *